United States Patent [19]
Al-Ali

[11] Patent Number: 5,509,424
[45] Date of Patent: Apr. 23, 1996

[54] CONTINUOUS CARDIAC OUTPUT MONITORING SYSTEM

[75] Inventor: Ammar Al-Ali, Costa Mesa, Calif.

[73] Assignee: Aws Salim Nashef, Huntington Beach, Calif.

[21] Appl. No.: 188,274

[22] Filed: Jan. 28, 1994

[51] Int. Cl.⁶ .................................................. A61B 5/028
[52] U.S. Cl. .......................................... 128/692; 128/713
[58] Field of Search ..................................... 128/691–692, 128/713, 736, 668, 687

[56] References Cited

U.S. PATENT DOCUMENTS

| | | |
|---|---|---|
| 3,359,974 | 10/1963 | Khalil . |
| 4,217,910 | 8/1980 | Khalil . |
| 4,236,527 | 12/1980 | Newbower et al. . |
| 4,240,441 | 12/1980 | Khalil . |
| 4,300,391 | 11/1981 | Eiermann . |
| 4,319,483 | 3/1982 | Durham, Jr. et al. . |
| 4,616,505 | 10/1986 | Jouwsma . |
| 4,685,470 | 8/1987 | Sekii et al. . |
| 4,745,805 | 5/1988 | Granier . |
| 4,783,996 | 11/1988 | Ohta et al. . |
| 4,817,624 | 4/1989 | Newbower . |
| 4,841,981 | 6/1989 | Tanabe et al. . |
| 4,941,475 | 7/1990 | Williams et al. . |
| 4,979,514 | 12/1990 | Sekii et al. . |
| 5,003,490 | 3/1991 | Castelaz et al. . |
| 5,056,526 | 10/1991 | Khalil . |
| 5,092,343 | 3/1992 | Spitzer et al. . |
| 5,121,443 | 6/1992 | Tomlinson . |
| 5,174,299 | 12/1992 | Nelson ..................................... 128/692 |
| 5,217,019 | 6/1993 | Hughes . |
| 5,243,988 | 9/1993 | Sieben et al. . |
| 5,247,584 | 9/1993 | Krogmann . |
| 5,261,411 | 11/1993 | Hughes . |
| 5,373,850 | 12/1994 | Kohno et al. ........................... 128/692 |

FOREIGN PATENT DOCUMENTS

| | | |
|---|---|---|
| 0235811 | 3/1987 | European Pat. Off. . |
| 2112767 | 7/1972 | France . |
| 2411392 | 7/1979 | France . |
| WO8911083 | 11/1989 | WIPO . |
| WO9117703 | 11/1991 | WIPO . |

OTHER PUBLICATIONS

"Catheterization of the Heart in Man with Use of a Flow–Directed Balloon–Tipped Catheter"; H. J. C. Swan, William Ganz, James Forrester, Harold Marcus, George Diamond and David Chonette; The New England Journal of Medicine; Aug. 27, 1970.

"Determination of Cardiac Output in Man by a New Method Based on Thermodilution"; H. H. Khalil; Preliminary Communications, Jun. 22, 1963.

"Continuous Thermal Measurement of Cardiac Output"; James H. Philip, Michael C. Long, Michael D. Quinn and Ronald S. Newbower; IEEE Transactions on Biomedical Engineering, vol. BME–31, No. 5, May 1984.

"Thermal Method for Continuous Blood–Velocity Measurements in Large Blood Vessels, and Cardiac–Output Determination"; A. L. Delaunois; Medical and Biological Engineering; Mar. 1973.

"A Cardiac Output Estimation Algorithm for a Catheter–Based Cold–Fluid Heat Exchanger System"; Fred K. Forster, John Y. J. Yan and Royce W. Johnson; 1993 IEEE.

*Primary Examiner*—Angela D. Sykes
*Attorney, Agent, or Firm*—Knobbe, Martens, Olson & Bear

[57] ABSTRACT

A cardiac catheter continuously monitors cardiac output within an artery. One temperature sensor measures native blood temperature within the artery, while another temperature sensor measures the temperature of a thermal coil which is in thermal contact with the blood stream. The temperature signals are provided as inputs to a monitoring system which includes isolators, filters, and data processing circuits. A temperature difference signal over time is generated between the native blood temperature and the thermal coil temperature. First and second derivatives are taken of the temperature difference signal and selected features are extracted from the three waveforms. The extracted features are used as to calculate cardiac output. In the present case, a neural network processor is utilized to provide accurate cardiac output measurements based upon the extracted features.

7 Claims, 10 Drawing Sheets

CONTINUOUS CARDIAC OUTPUT MONITORING SYSTEM

BACKGROUND OF THE INVENTION

1. Field of the Invention

The present invention relates to a catheter for continuously measuring cardiac output by means of a cardiac catheter with a temperature sensing device.

2. Description of the Related Art

In order to measure cardiac output, the volumetric rate at which blood is pumped through the heart, the conventional practice is to employ an indicator dilution method. Thermodilution, which is one-of the indicator dilution methods available, involves injecting a cooled or heated solution directly into the flow of blood and subsequently measuring the temperature of the blood at some known distance downstream from the place where the solution is injected.

One disadvantage associated with the thermo-dilution method is that measurement of cardiac output is performed intermittently and not continuously. Moreover, the frequency of performing the procedure is limited because of the dilution of the patient's blood and the associated increase in fluid burden. In addition, the thermo-dilution method involves an increased risk of infection to the patient from contaminated injectate fluid or injectate syringes.

In an attempt to overcome these disadvantages, one device, described in U.S. Pat. No. 4,841,981, entitled "Catheters for Measurement of Cardiac Output and Blood Flow Velocity," measures the cardiac output according to the conventional thermo-dilution technique, and subsequently calculates blood flow velocity by means of a blood temperature sensing thermistor and a self-heating thermistor. Because the blood flow velocity multiplied by the cross-sectional area of the pulmonary artery is equal to the cardiac output, the cross-sectional area of the pulmonary artery may be determined once the cardiac output has been determined by means of the thermo-dilution method. After the thermo-dilution method has been performed once, subsequent cardiac output is determined using the velocity measurement multiplied by a constant obtained using the initial thermo-dilution measurement.

This method may provide continuous measurement of cardiac output provided that the cross sectional area of the pulmonary artery at the self-heated, measuring thermistor remains substantially constant. However, it has been observed that the parameter representing the blood vessel cross-sectional area, in fact, varies with time. Thus, in order to account for this variation, recalibration is carried out periodically by means of the thermo-dilution method in this device. In addition, the measuring location of the catheter may move into a region of the pulmonary artery having a different cross-sectional area. If the catheter so moves, the velocity calculation method provides inaccurate results until a new calibration is completed using thermo-dilution measurements. Finally, because calibration involves a conventional thermo-dilution cardiac output measurement, the risk of infection and fluid burden from increased fluid volume are still present.

Thus, although some attempts have been made to provide continuous monitoring of cardiac output, these previous devices are susceptible to inaccuracies in measuring cardiac output. Furthermore, these devices may place an undue cardiac burden upon the patient and increase the risk of infection.

SUMMARY OF THE INVENTION

The present invention involves a method and apparatus for continuously calculating cardiac output without the introduction of additional volume into a patients vascular system. No infusate is required. The present invention also involves a method and apparatus for continuously calculating cardiac output without requiring the chilling of the patients blood. The cardiac monitoring apparatus and method of the present invention determines cardiac output based upon selected features derived from a temperature difference signal. The temperature difference signal is produced by subtracting the average native blood temperature detected at a proximal temperature sensor from the temperature of a heating coil detected by a distal temperature sensor. The heating coil is cooled by the blood as blood flows past the heating coil. According to a preferred embodiment of the present invention, first and second derivatives of the temperature difference signal are also utilized in the calculation. Several features are extracted from each of the three waveforms and processed to obtain cardiac output. In the present embodiment, the features extracted from the temperature difference signal and from the first and second derivatives of the temperature difference signal are provided as an input vector to a neural network processor to provide an output indicative of cardiac output.

One aspect of the present invention involves an isovolemic method of detecting volumetric flow rate of a liquid within a body lumen. The method is also accomplished without the necessity of chilling the liquid within the body lumen. The method comprises a number of steps. A first temperature of a heat transfer device which is in thermal contact with the liquid in the body lumen is detected. The first temperature varies over time with the flow rate of the liquid past the heat transfer device. A second native temperature of the liquid is detected, and a temperature difference signal over time based upon the first and second temperatures is generated. In one embodiment, the liquid in the body lumen is blood with a pulsatile flow characteristic and the volumetric flow rate is cardiac output.

Advantageously, the first and second derivatives of the temperature difference signal are calculated and a plurality of preselected features are extracted from the temperature difference signal, the first derivative signal and the second derivative signal. Based upon the features extracted, the volumetric flow rate is calculated. In the present embodiment, the volumetric flow rate is calculated using the preselected features as inputs for a multi-layer, artificial neural network. In one embodiment, the preselected features include one or more of the following features from the temperature difference signal: the frequency, the pulse time, the average temperature difference, the cooling area, the heating area, the cooling time and the heating time. With respect to the first and second derivative signals, exemplary features are the positive area in the first derivative of the signal, the negative area in the first derivative of the signal, the time of the positive area in the first derivative of the signal, the time of the negative area in the first derivative of the signal, the value of the maximum point of the first derivative of the signal, the value of the minimum point of the first derivative of the signal, positive area in the second derivative of the signal, negative area in the second derivative of the signal, time of the positive area in the second derivative of the signal, time of the negative area in the second derivative of the signal, the value of the maximum point of the second derivative of the signal, and the value of the minimum point of the second derivative of the signal.

Other ratios between these features are also calculated in one embodiment.

Still another aspect of the present invention involves an apparatus for measuring the volumetric flow rate of a liquid within a body lumen, the volumetric flow rate preferably being the cardiac output. The apparatus comprises a heat transfer device which is in thermal communication with the liquid in the body lumen. The heat transfer device is responsive to a low power signal to heat the heat transfer device to a first temperature. The first temperature varies with the pulsatile flow of the liquid. A first temperature sensor is in thermal contact with the heat transfer device and measures the temperature of the heat transfer device. The first temperature sensor has a first output with a first output signal indicative of the temperature of the heat transfer device. A second temperature sensor is in thermal contact with the liquid to measure the native temperature of the liquid. The second temperature signal has a second output having the second output signal indicative of the native temperature of the liquid. A comparator responds to the first output signal and the second output signal to provide a temperature difference signal representing the difference in temperature between the native temperature of the liquid and the temperature of the heat transfer device. A signal processing unit is coupled to the comparator and extracts pre-specified features from the temperature difference signal. In the present embodiment, the pre-specified features are processed with a neural network processor in order to calculate the volumetric flow rate of the liquid. Preferably, the volumetric flow rate is cardiac output. In one embodiment, the signal processing unit also calculates first and second derivatives of the temperature difference signal and extracts additional pre-specified features from the derivative signals. These pre-specified features from the derivative signals are also passed through the neural network processor.

In one embodiment, the heat transfer device comprises a thermal coil with a thermally conductive layer interposed between the thermal coil and the first temperature sensor. Preferably, the first and second temperature sensors comprise high accuracy thermistors.

In one embodiment, the neural network processor comprises a recurrent, multi-layer neural network. In another embodiment, the neural network comprises a back-propagation, multi-layer neural network. Advantageously, the neural network comprises nonlinear activation functions for at least one hidden layer and linear activation functions for an input and an output layer.

DETAILED DESCRIPTION OF THE PREFERRED EMBODIMENTS

The cardiac monitoring system of the present invention includes detecting and monitoring equipment, as well as a method and apparatus for examining the detected and monitored signals, to provide an indication of cardiac output. In general, a catheter located in an artery is utilized to obtain a temperature difference signal between a temperature ($T_1$) of a heat transfer device in thermal contact with blood and a native blood temperature ($T_2$). The temperature difference signal is generated over time to form a temperature difference waveform. First and second derivatives of the temperature difference waveform are calculated. A plurality of features are extracted from the temperature difference waveform, the first derivative waveform, and the second derivative waveform. The features are then processed to obtain the cardiac output for the patient. In the present embodiment, the features form an input vector for a neural network processor trained to correlate the features to cardiac output.

Advantageously, the cardiac monitoring system of the present invention is isovolemic. In other words, the calculation of cardiac output according to the present invention does not require the introduction of fluid to the patients vascular system. In addition, the cardiac monitoring system of the present invention does not require chilling of the patient's blood. Accordingly, the cardiac monitoring system of the present invention can significantly reduce the risk of infection to the patient and reduce the fluid burden placed on the patient by methods that require introduction of an infusate into the patient's vascular system. The principles and details of operation are apparent with the following detailed description of the invention.

Figure 1:
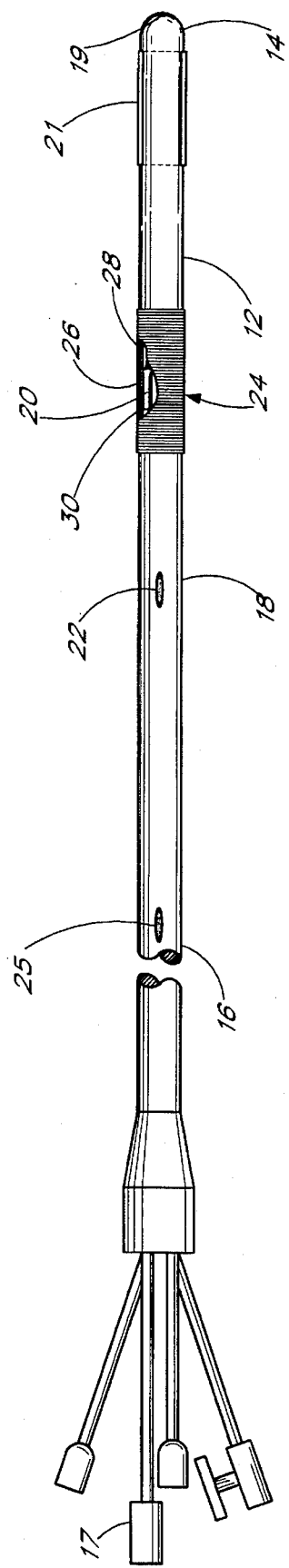
FIG. 1 illustrates a cardiac output monitor catheter constructed in accordance with the teachings of the present invention.

FIG. 1 shows a schematic representation of an exemplary cardiac catheter 10 for measuring cardiac output in accordance with the present invention. The cardiac catheter 10 includes a catheter body 12 having a distal end 14, a proximal portion 16, and an outer surface 18. A first or distal temperature sensor 20 is positioned apart from a second or proximal temperature sensor 22. In one embodiment, the distal and proximal temperature sensors 20, 22 comprise thermistors.

The proximal temperature sensor 22 measures undisturbed or native blood temperature ($T_2$). Therefore, the proximal temperature sensor 22 need not be located in close proximity to the distal temperature sensor 20. The proximal temperature sensor 22 need only be located and configured to measure native blood temperature. However, it is preferable to provide the proximal temperature sensor 22 at a reasonable proximity to the heat transfer device 24 due to the possible slight variations in blood temperature if the proximal temperature sensor 22 measuring native blood temperature was located elsewhere in the body. In the embodiment depicted in FIG. 1, the proximal temperature sensor 22 is positioned proximal from the distal temperature sensor 20 along the catheter body 12. In a preferred embodiment, the proximal temperature sensor 22 is positioned on or embedded along the outer surface 18 of the catheter body 12 to be in thermal contact with the blood stream.

The catheter 10 further comprises a pressure monitoring port 19 in fluid communication with an internal lumen of the catheter 10. The catheter 10 further comprises an inflation balloon 21 in fluid (including air) communication with an inflation balloon lumen internal to the catheter 10. The inflation balloon 21 is well understood in the art and commonly present with conventional thermo-dilution cardiac catheters. The pressure monitoring port 19 can be utilized for pulmonary artery pressure (PAP) measurements, for wedge pressure measurements (PAOP), and for injection of fluids into the pulmonary artery, as well understood in the art. The catheter 10 in the present invention can also include a proximal injectate port 25 which is proximal to the proximal temperature sensor 22. The proximal injectate port 25 can be utilized in conjunction with the proximal temperature sensor 22 to perform thermo-dilution cardiac output measurements as well understood in the art.

The distal temperature sensor 20 is in thermal communication with a heat transfer device 24. In the present embodiment, the heat transfer device 24 is radially disposed about the catheter body 12. Alternatively, the heat transfer device 24 is embedded along the outer surface 18 of the catheter body 12 such that the heat transfer device does not significantly protrude from the catheter body 12.

Figures 2, 3:
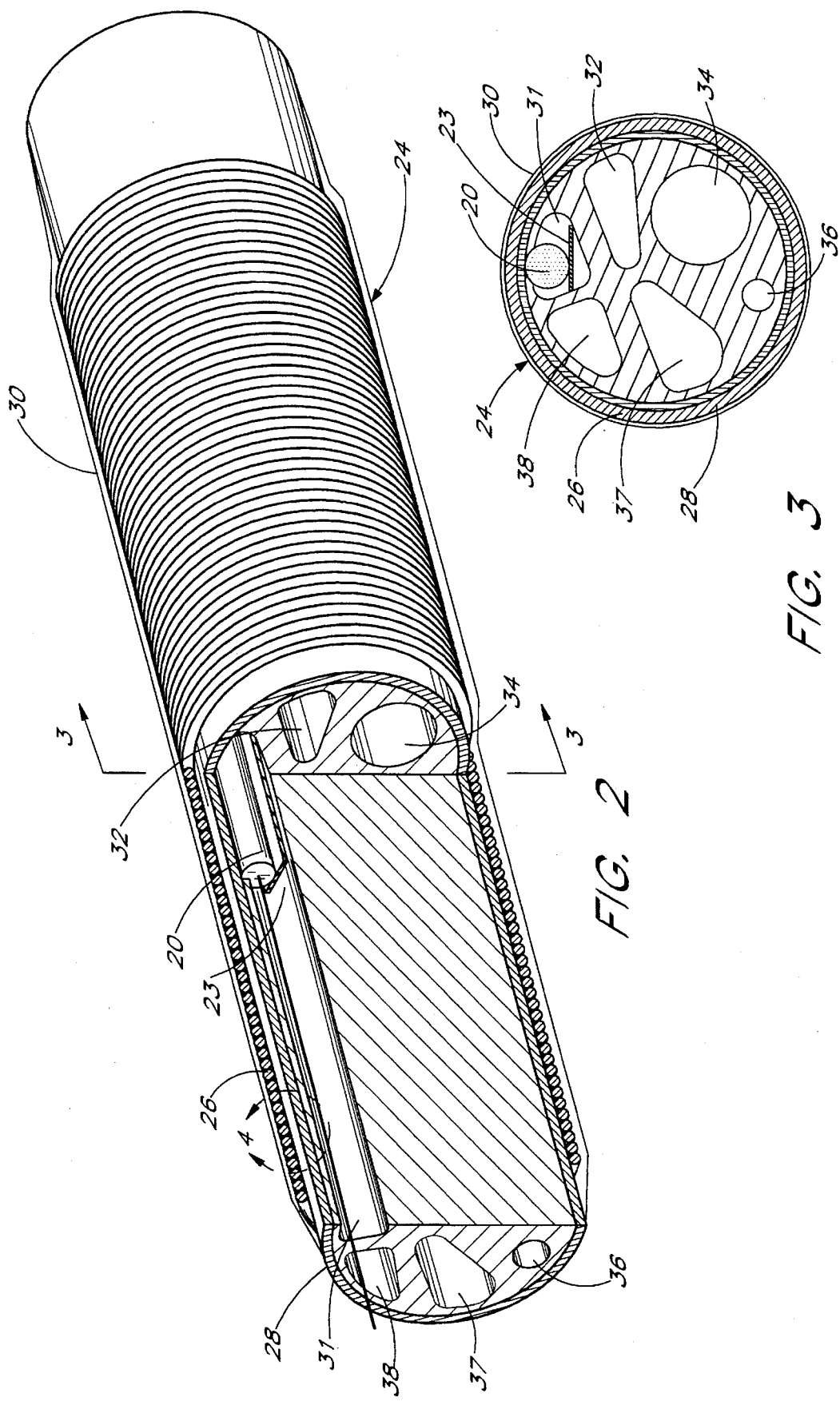
FIG. 2 is an illustration of a cut-away view of a heat transfer device and distal temperature sensor in accordance with the present invention.
FIG. 3 is an end cross-sectional view of the catheter at the cut-away location of FIG. 2.

FIG. 2 is a perspective view of a portion of the cardiac catheter 10, and illustrates the exemplary heat transfer device 24 constructed in accordance with the present invention. In the present embodiment, the heat transfer device 24 is generally tubular. The generally tubular heat transfer device 24 of FIG. 2 comprises an electrically insulated (from the bloodstream) heating or thermal coil 26, a heat conducting material or layer 28 and an insulating layer 30. The thermal coil 26 is in electrical communication with a current driver (not shown in FIG. 2). The thermal coil 26 is sandwiched between the heat conducting layer 28 and the insulating layer 30. The thermal coil 26 is in thermal communication with the blood stream when the catheter 10 is positioned in a vascular lumen.

The embodiment of the heat transfer device 24 depicted in FIG. 2 is particularly advantageous because of the average or equilibrium temperature that is provided. The heat transfer device 24 is advantageously configured to dissipate heat radially from the thermal coil 26 in an efficient manner. If the heat transfer device 24 were simply on one side of the catheter body 12, the temperature of the heat transfer device 24 would depend upon the proximity of the heat transfer device to the vascular wall. By providing a generally tubular heat transfer device 24 extending about the catheter body 12, the temperature of the heat transfer device 24 is less dependent upon the proximity to a vascular wall.

A preferred position for the distal temperature sensor 20 is within the proximal and distal longitudinal boundaries of the heat transfer device. Longitudinally centering the distal temperature sensor 20 with respect to the heat transfer device 24 is advantageous in further taking into account the average heat transfer to the blood flowing past the heat transfer device 24.

The distal temperature sensor 20 is preferably embedded along the catheter body surface 18 and juxtaposed or adjacent to the heat transfer device 24. Advantageously, the distal temperature sensor 20 is in thermal, as well as physical, contact with the heat conducting layer 28. The cut-away in FIG. 2 further depicts a positioning layer 23. The positioning layer 23 is disposed adjacent the distal temperature sensor 20 opposite the heat conducting layer 28. The positioning layer 23 is advantageously fabricated from a thin latex sheet and provides cushioning beneath the distal temperature sensor 20. The positioning layer 23 applies pressure to the distal temperature sensor 20 for improved thermal contact between the distal temperature sensor 20 and the heat conducting layer 28. The contact of the distal temperature sensor 20 with the heat conducting layer 28 continuously provides an indication of increase or decrease in heat dissipated by the thermal coil 26 into the blood flowing past the thermal coil 26. As explained in further detail below, a decrease in the temperature at the distal temperature sensor 20 is attributed to an increase in heat dissipation resulting from an increase in blood flow past the thermal coil 26.

As discussed in further detail below, the distal and proximal temperature sensors 20, 22 are in electrical communication with a monitoring system via a proximal connection port 17. For ease of illustration, the monitoring system is not shown in the general illustration of FIG. 1. Other connection ports for the fluid lumens in the catheter are provided as depicted in FIG. 1.

FIG. 3 is an end cross-sectional view of the catheter 10 at the location of the cut-away in FIG. 2. This embodiment of the catheter 10 has six lumens such as a conventional six-lumen, Swanz-Ganz type catheter. The six lumens comprise a distal temperature sensor lumen 31, a thermal coil lead lumen 32, a pulmonary artery distal infusion lumen 34, an inflation balloon lumen 36, a proximal injectate lumen 37, and a proximal temperature sensor lumen 38.

In one embodiment, the distal temperature sensor 20 is positioned within the distal temperature sensor lumen 31 and embedded in the catheter body 12. The positioning layer 23 is positioned within the distal temperature sensor lumen 31 to hold the distal temperature sensor 20 against the heat conducting layer 28. The distal temperature sensor lumen 31 also carries the electrical connections between the distal temperature sensor 20 and the proximal connection port 17.

The proximal temperature sensor lumen 38 carries the electrical connections between the proximal temperature sensor 22 and the proximal connection port 17. The proximal injectate lumen 37 is in fluid communication with the proximal injectate port 25. The proximal injectate port 25 can be utilized to execute thermo-dilution measurements of cardiac output, as well understood in the art. The thermal coil lead lumen 32 carries the electrical connections to the thermal coil 26, and the pulmonary artery distal infusion lumen 34 is in fluid communication with the pulmonary artery pressure monitoring port 19 (FIG. 1). The inflation balloon lumen 36 is in fluid communication with the inflation balloon 21 for inflation and deflation thereof. As well understood in the art, when the inflation balloon 21 is inflated, it allows for proper flotation of the catheter 10 into the desired arterial locations.

Figure 4:
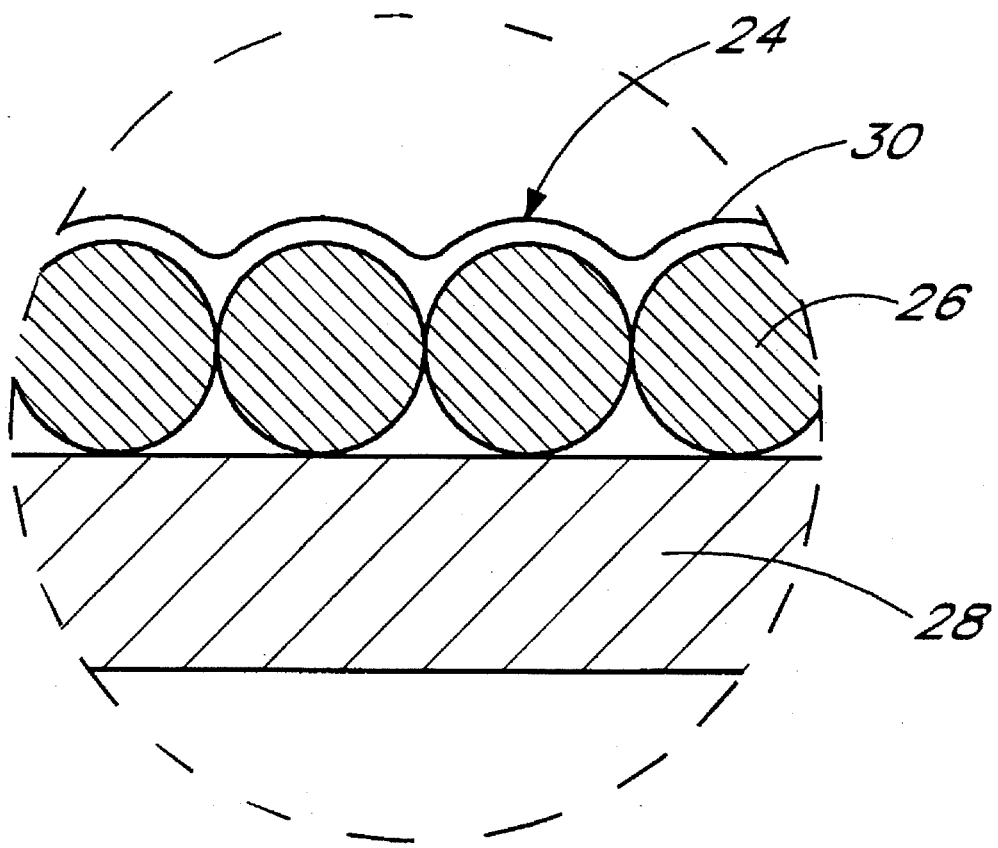
FIG. 4 is an enlarged longitudinal cross-sectional view taken from the portion indicated as area 4—4 of FIG. 2.

FIG. 4 depicts an enlarged portion of the region 4—4 in FIG. 2. As depicted in FIGS. 1–4, the thermal coil 26, the heat conducting layer 28, and the insulating layer 30 are concentric layers which form the tubular configuration of heat transfer device 24. Moreover, the heat conducting layer 28 is in thermal contact with the distal temperature sensor 20 and the thermal coil 26 such that the distal temperature sensor 20 can detect the temperature of the thermal coil 26.

The choice of materials for each of the elements of heat transfer device 24 and for the temperature sensors 20, 22 is dependent upon the range of fluid volume flow, the heat capacity of the fluid, the fluid temperature, and the temperature differential described below.

In the present embodiment, the thermal coil 26 is preferably formed with each turn of the coil in contact with adjacent turns. The dimensions of the filament for the thermal coil 26 can vary, and depends upon the range of fluid volume, the heat capacity of the liquid, the fluid temperature, and the temperature differential. In one embodiment, the thermal coil 26 comprises a high resistance nickel alloy filament about 2 feet to 6 feet in length with a diameter of from about 0.002 inches to about 0.005 inches. Once the thermal coil 26 is wound on the heat conducting layer 28, the coil has a selected overall length. In one preferred embodiment, the selected length, measured longitudinally along the length of the catheter body 12, is from about 0.2 inches to about 0.5 inches.

As further illustrated in FIGS. 1–4, in one preferred embodiment, the heat conducting layer 28 is coextensive with the insulating layer 30, and the thermal coil 26 has a shorter overall length than the heat conducting layer 28 and the insulating layer 30. In a particularly preferred embodiment, the heat conducting layer 28 is a gold plated copper bushing having a length of from about 0.3 inches to about 0.6 inches, an internal diameter of from about 0.07 inches to about 0.095 inches, and a wall thickness of from about 0.002 inches to about 0.006 inches.

The insulating layer 30 is preferably a thermally conductive, not moisture absorbing, biocompatible and blood compatible material such as a hydrophobic biocompatible polymeric material. The thickness of the insulating layer 30 is thick enough to electrically insulate and thin enough to dissipate small amounts of heat. The thickness of the insulating layer depends on the factors enumerated above for the heat transfer device 24 in general. In one embodiment, the insulating layer 30 has a thickness of less than 0.002 inches. It has also been found that the thickness of the insulating layer 30 is advantageously substantially uniform. In one preferred embodiment, the insulating layer is polyxylylene.

As briefly mentioned above, the distal and proximal temperature sensors 20, 22 can be thermistors, thermocouples, or any means known in the art for detecting temperature or temperature changes. The actual choice of temperature sensors is dependent upon design configurations and, particularly, the range of temperature and temperature differentials which are under consideration. Preferably, the temperature sensors 20, 22 are thermistors of the type which detect small changes in temperature, on the order of less than 0.05° C. with precision and reliability. Those skilled in the art will appreciate that combinations of different types of temperature sensors can be utilized as the distal and proximal temperature sensors 20, 22.

For purposes of measuring cardiac output, the catheter body 12 is preferably dimensioned for placement within a patient vascular lumen having flowing blood. Such vascular lumens include, but are not limited to, the pulmonary artery, the right ventricle, the right atrium, the vena cava, the aorta, and other major arteries. Advantageously, suitable catheter bodies can be any of numerous catheters which are commercially available. For example, catheters known in the art for providing pulmonary artery pressure (PAP), wedge pressure (PAOP), and central venous pressure (CVP) or $SVO_2$ can incorporate the heat transfer device 24 and the temperature sensors 20, 22 of the present invention without interfering with catheter function and insertion.

The catheter of the present invention can be fabricated using common assembling techniques available to those skilled in the art of designing and forming catheters for medical use. The thermistors are conveniently and advantageously mounted on or embedded in the outer surface 18 of the catheter 10 using well known methods such as adhesive bonding. A suitable heat transfer device 24 can be constructed by forming a thermal coil over the heat conducting layer 28. The insulated layer 30 can then be formed over the exposed thermal coil 26. Finally, the assembled heat transfer device is slipped over the catheter body 12 and secured to the catheter body 12 juxtaposed to and in alignment with the distal temperature sensor 20.

As mentioned, in order to provide cardiac output information to a user, the present invention additionally involves a system which further comprises instrumentation for controlling and supplying power, performing monitoring, and displaying information.

Figure 5:
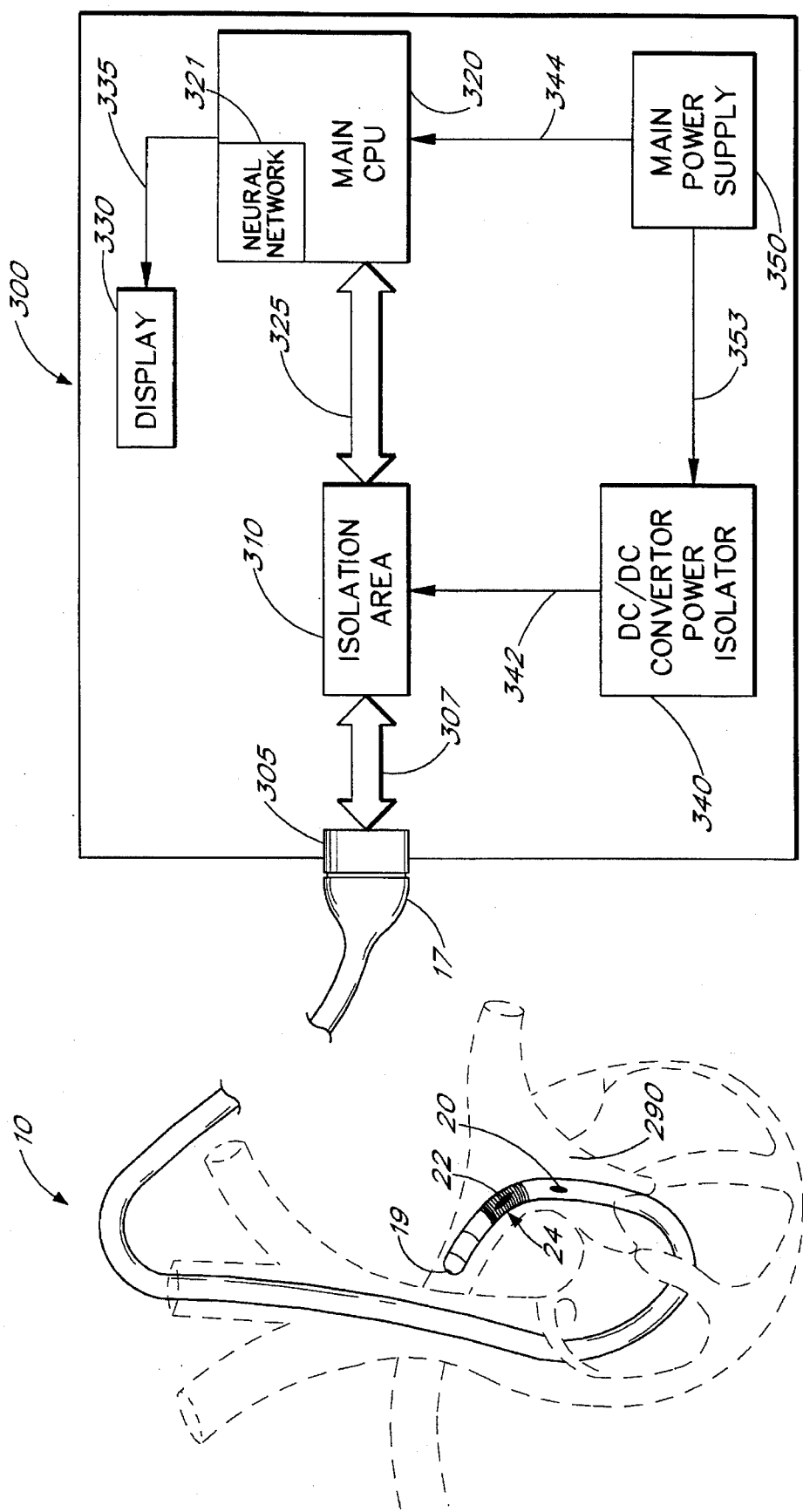
FIG. 5 is a schematic representation of the cardiac catheter as positioned within the pulmonary artery and connected to a monitoring system in accordance with the present invention.

FIG. 5 illustrates a block diagram of a monitoring system 300 for monitoring cardiac output in conjunction with the use of the cardiac catheter 10. The proximal connector 17 of the catheter 10 connects to the monitoring system 300 via a connection port 305. The connection port 305 electrically communicates with an isolation area 310 via a bidirectional bus 307. The isolation area 310 communicates with a main CPU 320 via a bidirectional communication bus 325. The main CPU 320 may, for example, comprise an INTEL 486 microprocessor unit or other central processing device with supporting resources. In the present embodiment, the main CPU 320 executes a neural network 321. The main CPU 320 connects to a display screen 330 via a bus 335. The display screen 330 may, for example, be a touch screen assembly well understood in the art. The isolation area 310 receives power from a DC to DC converter/power isolator 340 via signal lines 342. The main CPU 320 receives power from the main power supply 350 over signal lines 344. The main power supply 350 also provides power to the DC to DC converter/power isolator over signal lines 353. The DC to DC converter/power isolator 340 supplies power at five-volts DC and fifteen-volts DC to the isolation area 310 in one embodiment. Advantageously, the isolator 340 provides electrical isolation, as required, between the patient and the main power supply 344.

Figure 6:
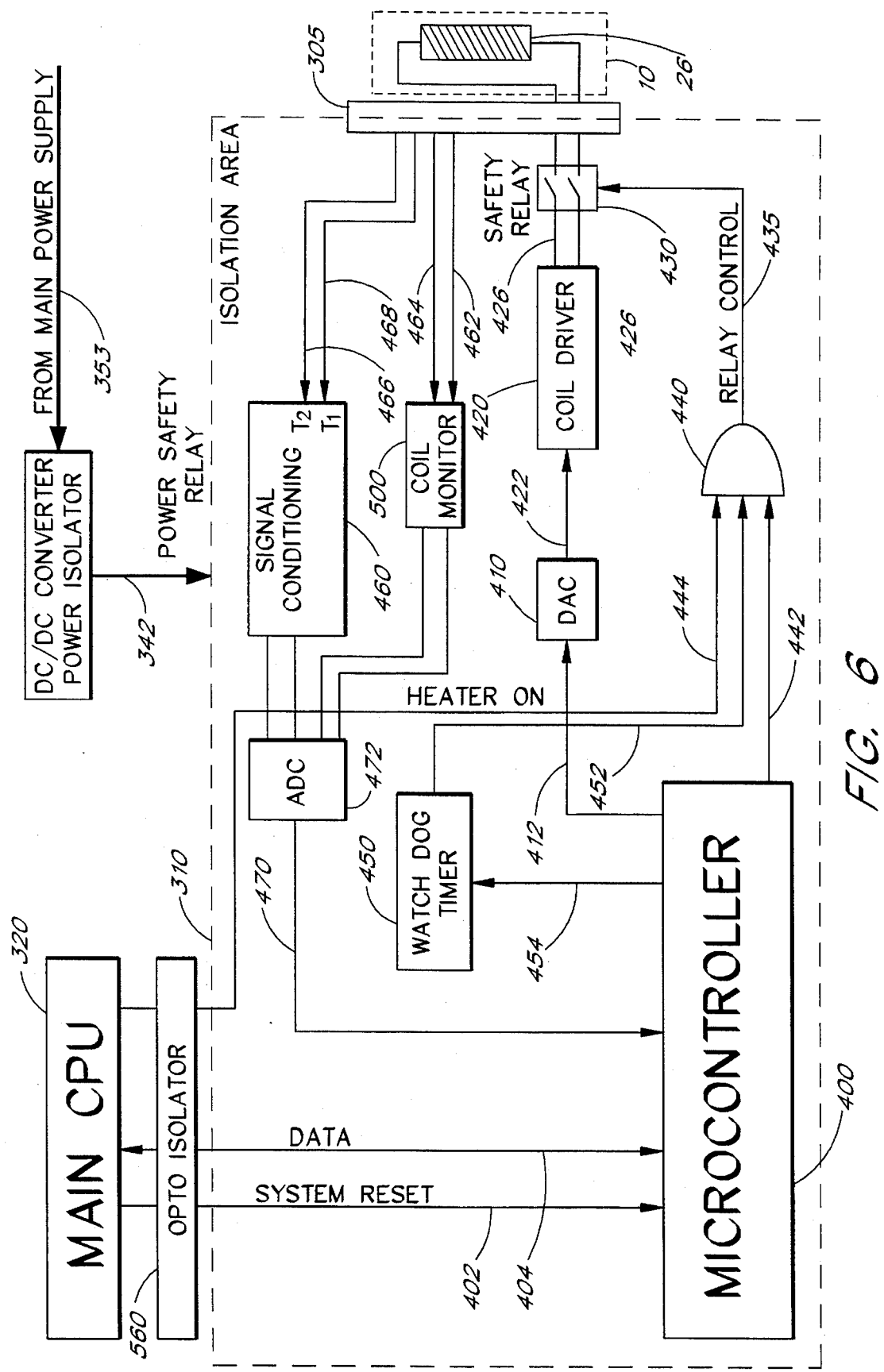
FIG. 6 is a functional block diagram depicting the monitoring system of FIG. 5 in greater detail.

The operation and the main structural and functional elements of the cardiac monitoring system 300 are described in greater detail with reference to FIG. 6 and 7. FIG. 6 depicts the monitoring system 300 in greater detail, and also depicts some safety mechanisms used within the cardiac monitoring system 300. As shown in FIG. 6, the main CPU 320 connects to a microcontroller 400 within the isolation area 310. In one embodiment, the microcontroller 400 comprises an INTEL 8031 microcontroller. Other microcontrollers are also suitable. Among other signal lines, the bidirectional communications bus 325 (see FIG. 5) includes a system reset line 402, whereby the main CPU 320 may reset the microcontroller 400, and a data bus 404, which allows the passage of cardiac monitoring data (and other data) between the microcontroller 400 and the main CPU 320. A digital-to-analog converter 410 is coupled to the microcontroller 400 via a signal line 412. The digital-toanalog converter 410 communicates with a coil driver 420 via a signal line 422. The coil driver 420 supplies current to the thermal coil 26 within the catheter 10 via electrical leads 426. A safety relay 430 is interposed between the thermal coil 26 and the coil driver 420 in order to prevent overheating or overdriving of the thermal coil 26.

The safety relay 430 is activated by a relay control line 435. The relay control line 435 constitutes the output of a AND-gate 440. The AND-gate 440 receives an input from the microcontroller 400 via a signal line 442, an input from the main CPU 320 via a heater-on signal line 444, and an input from a watch-dog timer 450 via a signal line 452. The watch-dog timer 450 is under the control of the microcontroller 400 via a signal line 454.

As well understood in the art, the watch-dog timer 450 is reset periodically by the microcontroller 400. The resetting occurs before the watch-dog timer times out. If the microcontroller 400 fails to reset the watchdog timer 450, this is indicative of some failure. When the watch-dog timer 450 times out, it causes an inactive signal on the output 452. This, in turn, causes an inactive output from the AND-gate 440 which opens the safety relay 430. Similarly, if the microcontroller 400 senses some malfunction in the system, the microcontroller can 400 directly open the safety relay via the control line 442. Finally, the main CPU 320 can also cut off power to the thermal coil 26 with the heater-on signal line 444.

A signal conditioning circuit 460 receives inputs from the catheter 10 over native blood temperature signal lines 466 and thermal coil temperature signal lines 468. The native blood temperature signal lines 466 are coupled to the proximal temperature sensor 22, while the thermal coil temperature signal lines 468 are coupled to the distal temperature sensor 20. By passing a small current through the proximal temperature sensor 22, the signal input on the signal lines 466 is representative of the native blood temperature $T_2$ within the pulmonary artery 290. Similarly, by passing a small current through the distal temperature sensor 20, the signal on the thermal coil temperature signal lines 468 is representative of the thermal coil temperature $T_1$.

In the signal conditioning circuit 460, the signal indicative of the thermal coil temperature $T_1$ and the signal indicative of the native blood temperature ($T_2$) are amplified, subjected to anti-aliasing to reduce distortion which may be due to sampling rates, and are normalized so that they fall with acceptable input signal ranges (e.g. 0–5 volts DC) receivable by the analog-to-digital converter 472. In the present embodiment, the anti-aliasing is completed with a low-pass filter having a cut-off frequency of approximately 15 Hz.

A coil monitor 500 receives further inputs from the catheter 10 on coil voltage signal lines 462 and coil current signal lines 464. The signals lines 462 and 464 carry signals for the coil voltage and coil current, respectively, for the thermal coil 26. As with the signals for the temperature sensors 20, 22, the coil voltage and coil current signals on the signal lines 462, 464, are subjected to similar signal conditioning in the coil monitor 500 (e.g., amplification, anti-aliasing and normalization for the analog-to-digital converter 472). The conditioned thermal coil temperature $T_1$, native blood temperature $T_2$, coil current, and coil voltage signals are provided by the signal conditioning circuit 460 and the coil monitor 500 as inputs to the analog-to-digital converter 472. The analog-to-digital converter 472 digitizes the signals and transmits them to the microcontroller 400 via signal lines 470. The analog-to-digital converter 472 is a multichannel converter which samples each channel in series and provides sample and hold capabilities as well understood in the art. In one advantageous embodiment, the analog-to-digital converter 472 is configured with a sampling rate of approximately 200 Hz and has a conversion time of approximately 100 microseconds per sample.

As signals are digitized within the analog-to-digital converter 472, the data is passed to the microcontroller 400. The microcontroller 400 communicates with the main CPU 320 via the bidirectional bus 325 (FIG. 5). As depicted in FIG. 6, the communication between the main CPU 320 and the microcontroller 400 are completed through an optoelectric isolation circuit 560. The optoelectric isolation circuit 560 provides isolation between the patient and the main CPU to maintain high isolation to prevent shock to the patient. Such isolation circuits are well understood in the art.

As mentioned above, the coil driver 420 provides current for the thermal coil 26. Advantageously, the coil driver 420 comprises gain and offset adjust circuitry (not shown) which receives input from the digital-to-analog converter 410 via the signal line 422. Preferably, the coil driver 420 further comprises current driver circuitry (not shown) which receives its input from the gain and offset adjust circuitry and provides a current output signal for the coil driver 420. The amount of current is selected by the microcontroller 400 via the digital-to-analog converter 410.

The current output signal of the coil driver 420 is provided as an input to the safety relay 430 via the signal lines 426. The safety relay 430, when closed, passes the current signal to the thermal coil 26 via the catheter connector 305.

The operation of the cardiac monitoring system 300 depicted in FIGS. 5 and 6 is described with reference to the data flow diagram of FIG. 7. The data flow diagram shown in FIG. 7 shows the main operations which are performed on detected data in accordance with the present invention.

In order to initiate the temperature readings for the thermal coil 26, the thermal coil 26 is activated. To accomplish this, the microcontroller 400 provides outputs to the digital-to-analog converter 410. The digital-to-analog converter 410 in turn provides a signal on its output 422 to the coil driver 420, which supplies power to the thermal coil 26. Accordingly, the signals from the microcontroller 400 to the digital-to-analog converter 410 are signals to control the amount of current the coil driver 420 provides to the thermal coil 26.

In a preferred embodiment, the microcontroller 400 sends control signals to the digital-to-analog converter 410 to cause the coil driver 420 to supply power to the thermal coil 26 in the range of 0.5 to 1.2 watts, and generally about 0.8 watts. The selection of the power level provided to the thermal coil 26 is maintained significantly constant in the present embodiment during measurement of the temperature difference between the proximal and distal temperature sensors 22, 20. The low power output by the coil driver 420 ensures that blood within the pulmonary artery 290 is not overheated, and that the thermal coil 26 does produce enough heat to cause damage to the artery wall.

Figure 7:
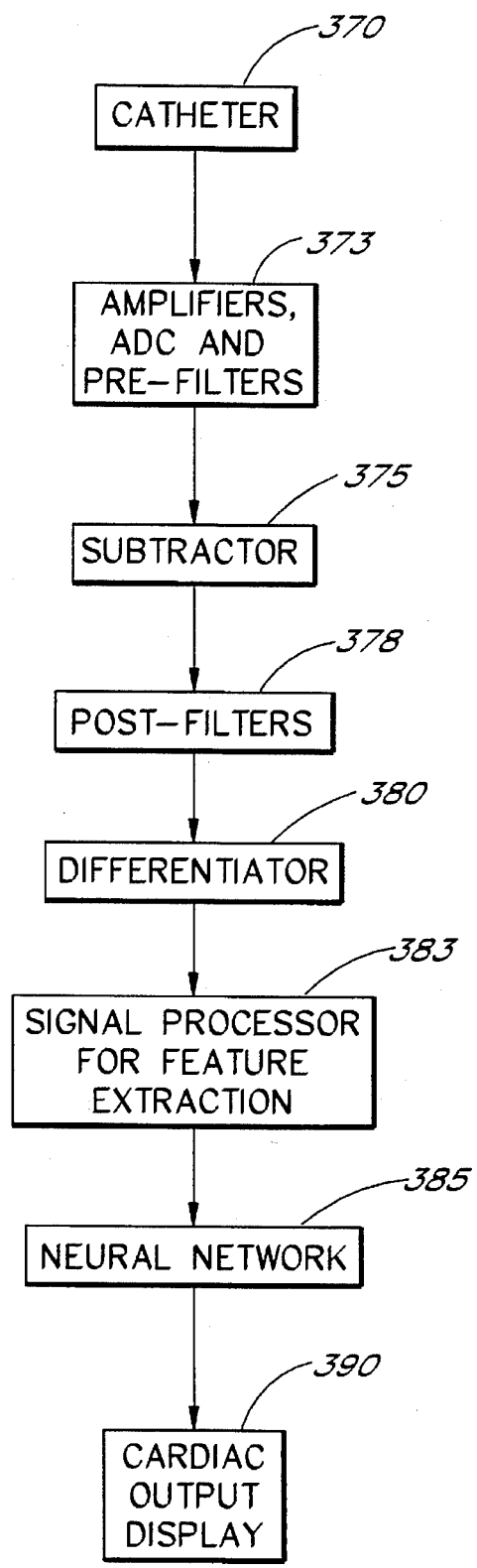
FIG. 7 is a data flow diagram which depicts the main operations used to process data in accordance with the present invention.

Within the catheter 10, represented by a block 370 in FIG. 7, the distal temperature sensor 20 measures the temperature ($T_1$) of the thermal coil 26 as heat is dissipated to the bloodstream while the proximal temperature sensor 22 measures the native blood temperature ($T_2$) within the pulmonary artery 290. Signals representative of the thermal coil temperature $T_1$ (detected by the distal temperature sensor 20) and the native blood temperature $T_2$ (detected by the proximal temperature sensor 22) are transmitted to the isolation area 310 via the connection port 305 and the bidirectional bus 307. In addition, signals representative of the voltage and current of the thermal coil 26 are transmitted to the isolation area 310 via the connection port 305 and the bidirectional bus 307. Within the isolation area 310, the input signals are amplified and pre-filtered with the signal conditioning circuit 460 and the coil monitor 500, as indicated by a block 373 in FIG. 7. The signals are subsequently provided to the analog-to-digital converter 472 to digitize the input signals. The isolation area 310 then transmits the signals to the main CPU via the bidirectional communications bus 325.

The coil current and coil voltage are primarily monitored for safety purposes to ensure that neither the voltage nor current output to the thermal coil 26 exceeds safe levels. If current within the thermal coil 26 exceeds safe levels, the output provided to the thermal coil 26 by the coil driver 420 is cut off by the safety relay 430. Additionally, if the microcontroller 400 senses that the coil current or coil voltage exceeds preestablished safety limits, the microcontroller 400 sends a signal to the digital-to-analog converter 410 to provide zero coil current to the thermal coil 26. This provides an additional level of safety.

The digitized data produced by the analog-to-digital converter 472 is provided as an input to the microcontroller 400. The microcontroller 400 performs basic data gathering operations and limited filtering operations. Specifically, in the present embodiment, the microcontroller 400 averages every four data samples for each provided signal. That is, every four temperature samples from the proximal temperature sensor 22 are averaged, every four temperature samples from the distal temperature sensor 20 are averaged, etc. Because the sampling rate of the analog-to-digital converter 472 is approximately 200 Hz, the frequency of digital samples output by the microcontroller 400 is approximately 50 Hz. It will be understood that 50 Hz is well above the Nyquist frequency required for the present application, and lower sampling rates may be desirable. The sampling rate of 50 Hz used in the present embodiment has been found to provide high resolution outputs, which are advantageous for purposes of data processing that occur within the main CPU 320.

The digitized and prefiltered temperature data are passed from the microcontroller 400 to the main CPU 320. Once the temperature signals have been amplified, digitized, and filtered within the isolation area 310, and the signals are passed to the main CPU 320, a difference is taken between the native blood temperature $T_2$ and the thermal coil temperature $T_1$ by comparing the digitized signals within the main CPU 320, as indicated by a subtractor block 375. The difference between the thermal coil temperature $T_1$ and the native blood temperature $T_2$, fluctuates with time as the blood is pumped more and less rapidly past the thermal coil 26. Thus, a time varying temperature difference waveform 600 (FIG. 8) is generated in the main CPU 320.

Within the main CPU 320, additional filtering operations occur, indicated by a post-filter block 378. Filtering primarily involves smoothing and averaging of the waveforms. Conventional noise removal filtering is also employed.

Derivatives are then taken of the time varying temperature difference waveform, as indicated by a differentiator block 380. Features are extracted from the time varying temperature difference waveform and the derivatives of the temperature difference waveform within the main CPU 320, as represented by a block 383. In the present embodiment, these features are used as inputs to an artificial neural network within the main CPU 320, indicated by a neural network block 385. The neural network determines the cardiac output. Finally, a signal indicative of the cardiac output is transmitted from the main CPU 320 to the display 330 via the bus 335, as indicated by a cardiac output display block 390 in FIG. 7.

Figure 8:
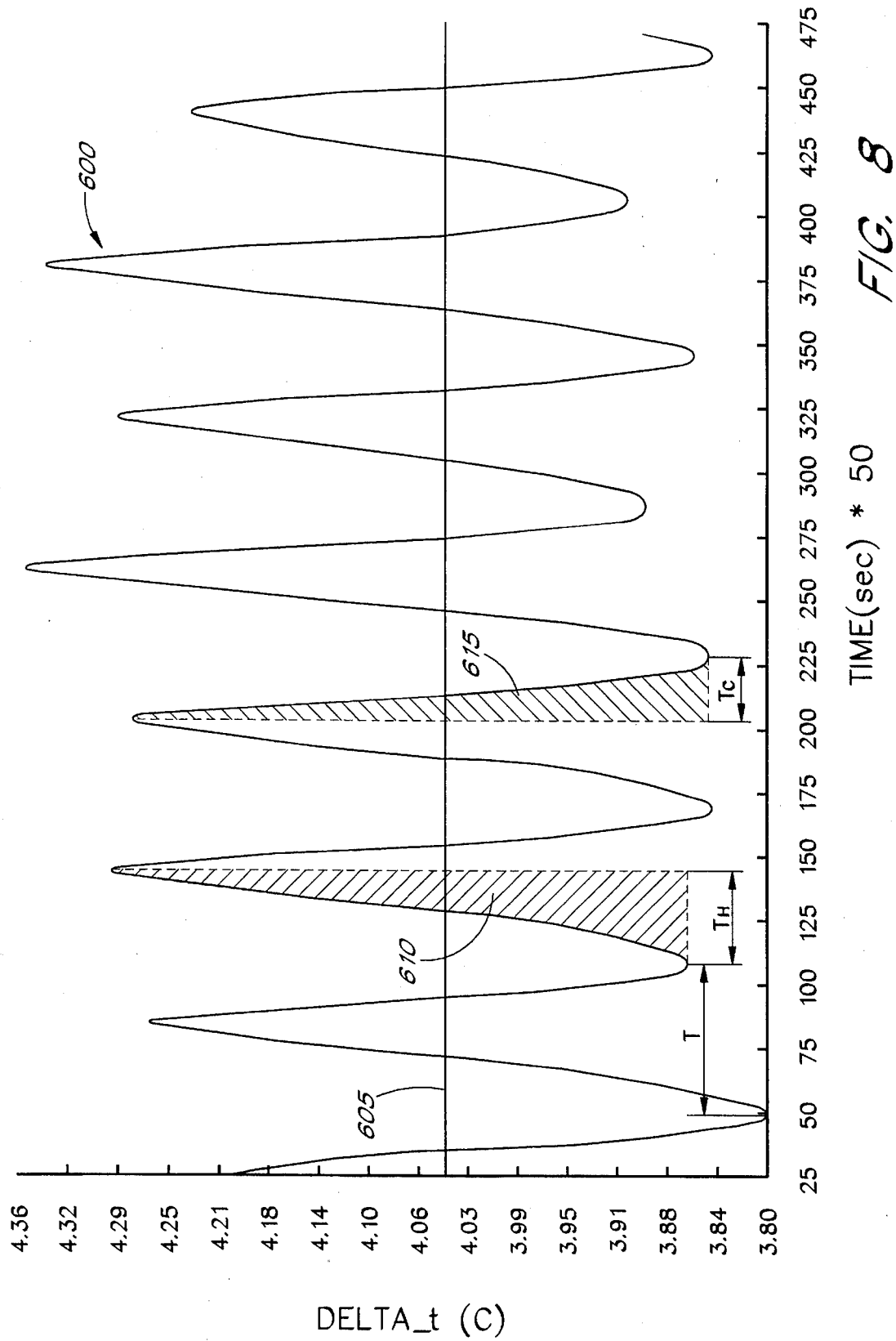
FIG. 8 is a graphical representation of the variation over time of the temperature difference between the temperatures sensed by the proximal and distal temperature sensors in the cardiac monitoring catheter of the present invention.
Figure 9:
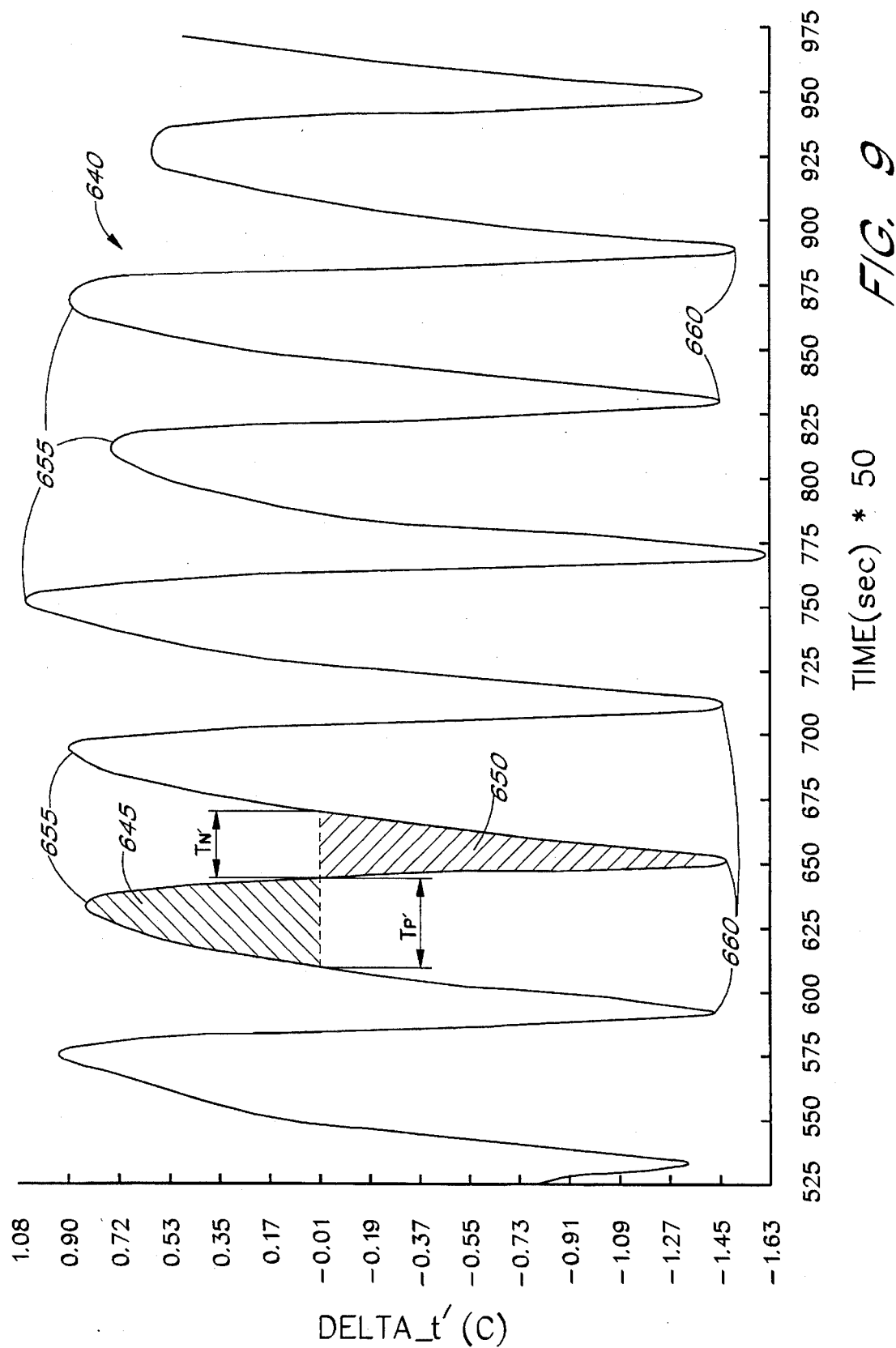
FIG. 9 illustrates a first derivative with respect to time of the waveform shown in FIG. 8.
Figure 10:
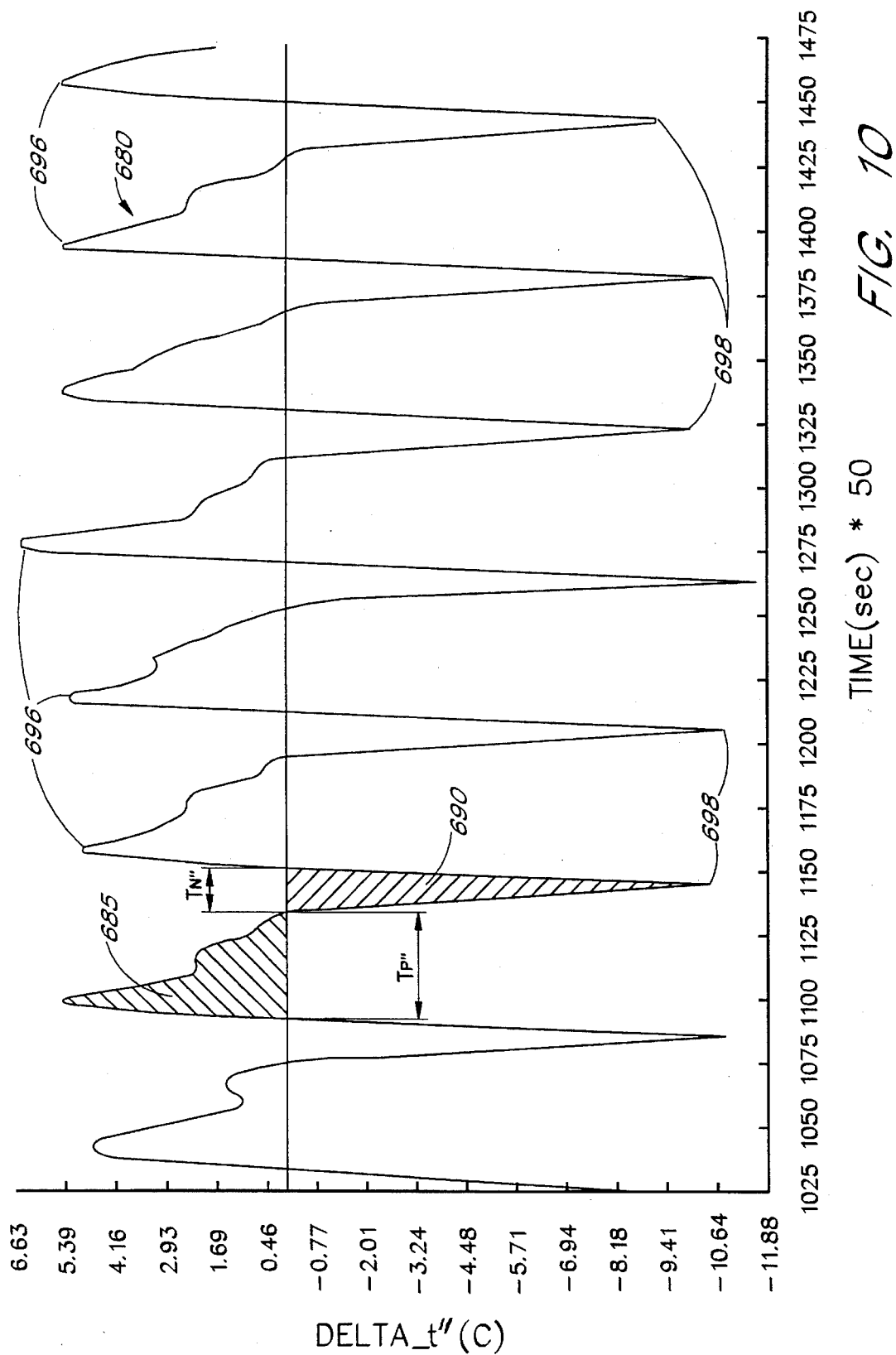
FIG. 10 illustrates a second derivative with respect to time of the waveform shown in FIG. 8.

FIGS. 8–10 depict signal waveforms derived from the temperature signals detected by the proximal and distal temperature sensors 22, 20. Specifically, the vertical axis in FIG. 8 represents the difference between the thermal coil temperature $T_1$ and the native blood temperature $T_2$. The horizontal axis represents elapsed time (in seconds, multiplied by 50). Thus, the waveform 600 of FIG. 8 is a temperature difference waveform as the temperature difference varies over time. A waveform 640 of FIG. 9 is the derivative with respect to time of the waveform 600 shown in FIG. 8. A waveform 680 of FIG. 10 is the second derivative with respect to time of the waveform 600 shown in FIG. 8.

Each of the waveforms 600, 640, 680 depicted in FIGS. 8–10 have been found to contain features which are useful in determining cardiac output. In the present embodiment, nineteen features are extracted from the waveforms 600, 640, 680, and several ratios of these features are calculate. These features and ratios, described in greater detail below, have been found to correlate to accurate cardiac output values when used as inputs to a trained neural network 321 within the main CPU 320. It should be noted, however, that other features may also provide additional useful input parameters for the neural network. Similarly, cardiac output may be calculated using less than all of the features. The nineteen features described below have been selected based upon experiments relating to the accuracy provided by those features, and upon believed relationships of these nineteen features to the kinetic energy generated by the heart.

The neural network 321 within the main CPU 320 comprises a back-propagation or recurrent multilayer neural network which is trained to provide the correct cardiac output measurement based upon the nineteen features or parameters input to the network and several ratios based upon these nineteen features. As understood in the art, the parameters input to a neural network are often referred to as the input vector. In other words, the input vector for the neural network in the present invention comprise the nineteen parameters described below and several values derived from the nineteen parameters. Training of the neural network is described with reference to FIG. 11 below.

FIG. 8 depicts the in temperature difference between the thermal coil temperature $T_1$ and the native blood temperature $T_2$. The native blood temperature $T_2$ remains substantially constant, while the thermal coil temperature $T_1$ varies with the movement of blood past the thermal coil 26. Thus, during times of high cardiac output, when blood movement is high, more heat is removed from the thermal coil 26. During times when the blood is relatively stationary about the thermal coil 26, less heat is removed from the thermal coil 26.

Consequently, the fluctuations observed in the temperature difference waveform 600 generally follow the pulse rate of the heart so that it is expected that the frequency of the waveform 600 may vary from about 0.6 Hz to 4 Hz (i.e., from about 36 beats per minute to 240 beats per minute). Thus, in order to fulfill the Nyquist frequency sampling requirement, a minimum sampling rate of 8 Hz should be employed by the analog-to-digital converter 540. (As explained above, the present embodiment utilizes an effective sample rate of 50 Hz).

For purposes of illustration, 7–8 cycles are shown in the ten second interval represented in FIG. 8. In the present embodiment, the cardiac output calculation is executed using ten seconds of waveform data. In other words, data is collected for ten seconds and an input vector representing the features extracted from the waveforms 600, 640 and 680 is presented to the neural network processor for calculation of the cardiac output. It should be noted that other periods are also appropriate. The ten-second interval has been found through experimentation to provide sufficient data for an accurate cardiac output determination, in accordance with the teachings of the present invention.

As stated above, in the present embodiment, nineteen features are extracted from the waveforms 600, 640, 680. The value assigned to each feature is based upon an averaging over the ten second interval. Thus, for example, if the feature to be extracted is the maximum value of the waveform within each cycle, and seven maximums occur within the given ten second interval, then seven sample values are averaged to obtain the desired feature value.

In accordance with the present invention, seven features are extracted from the temperature difference waveform 600. A brief listing of these features follows:

(1) Heart rate;
(2) Pulse time;
(3) Average temperature;
(4) Cooling area;
(5) Heating area;
(6) Cooling time; and
(7) Heating time.

Because the temperature difference waveform 600 generally follows the heart rate as explained above, the frequency of the waveform 600 may be used as an indication of the heart rate. For example, for the waveform 600 shown in FIG. 8, the heart rate is calculated to be approximately 0.83 Hz. The pulse period, represented in FIG. 8 by the interval T, is simply the inverse of the frequency of the waveform 600, that is, 1.2 seconds in the example of FIG. 8.

The Average temperature feature, which is an average temperature difference, is indicated by a line 605 in FIG. 8. The Average temperature feature represents the average value of the waveform 600 over the ten second interval. The cooling area feature is shown for one cycle of the waveform 600 as an area 615. The cooling area 615 is bounded on one side by the downwards sloping region in each cycle of the waveform 600, bounded on the other side by the vertical line drawn through the maximum point of the downwards sloping region, and bounded on the bottom by a horizontal line drawn through the minimum point of the downwards sloping region. The cooling area 615 is calculated using conventional integration techniques for each cycle. The heating area feature is shown for one cycle of the waveform 600 as an area 610.

The heating area 610 is bounded on one side by the upwards sloping region in each cycle of the waveform 600, bounded on the other side by the vertical line drawn through the maximum point of the upwards sloping region, and bounded on the bottom by a horizontal line drawn through the minimum point of the upwards sloping region. The heating area 610 is also calculated using conventional integration techniques. It should be noted here that only the areas cooling and heating within complete half cycles of the waveform 600 are factored into the ten second average. This insures that the overall average is not diminished by partial heating or cooling areas near the limits of the ten second averaging interval.

Finally, the heating time, represented over one cycle by the interval $T_H$ in FIG. 8, and the cooling time, represented over one cycle by the interval $T_C$ are extracted from the waveform 600. The heating time $T_H$ is measured as the time it takes the waveform 600 to pass from a minimum value to a maximum value within a given cycle. The cooling time $T_C$ is the time it takes to pass from a maximum value to a minimum value within a given cycle. The heating and cooling times are measured and averaged for each of the complete half cycles within the ten second interval to obtain the appropriate feature values.

A total of six features are extracted from the first derivative waveform 640 of FIG. 9. A brief listing of these features follows:

(1) Positive area in the first derivative of the signal;
(2) Negative area in the first derivative of the signal;
(3) Time of the positive area in the first derivative of the signal;
(4) Time of the negative area in the first derivative of the signal;
(5) The value of the maximum point of the first derivative of the signal; and
(6) The value of the minimum point of the first derivative of the signal.

As stated above, the waveform 640 represents the first derivative of the signal waveform 600 of FIG. 8. Thus, a shaded area 645 shown in FIG. 9, which constitutes the area beneath the positive portion of the waveform 640 within a given cycle, represents the positive area in the first derivative of the waveform 600 for one cycle of the signal 640. Similarly, a shaded area 650 which constitutes the area bounded by the negative portion of the waveform 640 for a given cycle represents the negative area in the first derivative of the waveform 600 for one cycle. Only the areas 645, 650 within complete half cycles of the waveform 640 are factored into the 10 second average to obtain feature values for both the positive and negative areas of the first derivative. This insures that the overall average will not be diminished by partial positive or negative areas near the limits of the 10 second averaging interval.

The time of the positive area in the first derivative of the signal is represented in FIG. 9 by the interval designated $T_P$. While the time of the negative area in the first derivative of a signal is represented in FIG. 9 by the interval designated $T_N$ for one cycle of the waveform 640. The interval $T_P$ is calculated as the time over which the waveform 640 remains positive within a given cycle of the waveform 640. Similarly, the interval $T_N$ is calculated as the time over which the waveform 640 is negative within one cycle of the waveform 640. The positive and negative times $T_P$ and $T_N$ are measured and averaged for each of the complete half cycles within the 10 second interval to obtain the appropriate average feature values.

Finally, two additional features extracted from the waveform 640 are the average maximum and minimum points of the derivative of the waveform 600. Because the waveform 640 is the first derivative of the waveform 600, maxima points 655 shown in FIG. 9 represent the maximum point of the first derivative of the waveform 600 while minima points 660 represent the values of minimum points of the first derivative of the waveform 600. To obtain the appropriate feature value, each of the maxima points within the 10 second interval are averaged as are each of the minima points within the 10 second interval.

As explained above, the curve 680 in FIG. 15 represents the second derivative of the temperature difference waveform 600 of FIG. 8. In the present embodiment, six features are extracted from the second derivative waveform 680 depicted in FIG. 10. A brief listing of these features follows:

(1) Positive area in the second derivative of the signal;

(2) Negative area in the second derivative of the signal;

(3) Time of the positive area in the second derivative of the signal;

(4) Time of the negative area in the second derivative of the signal;

(5) The value of the maximum point in the second derivative of the signal; and (6) The value of the minimum point of the second derivative of the signal.

An area 685 beneath the positive portion of the waveform represents the positive area in the second derivative of the waveform 600. Similarly, a shaded area 690 contained within one cycle of the negative portion of the waveform 680 represents the negative area in the second derivative of the waveform 600. For each complete half cycle of the waveform 680, a value is taken for the positive and negative areas 685, 690. The values within a given 10 second interval are averaged to provide the feature values for the positive area and the negative area of the second derivative of a signal.

An interval designated $T_P''$, shown in FIG. 15 indicates the time of the positive area in the second derivative of a signal for one cycle of the waveform 680. Likewise, an interval designated $T_N''$ indicates the time of the negative area in the second derivative signal for one cycle of the waveform 680. The interval $T_P''$ is calculated as the time over which the waveform 680 is positive within one complete cycle of the waveform 680, while the interval $T_N''$, is calculated as the time over which the waveform 680 is negative within one complete cycle of the waveform 680. The values of $T_P''$, and $T_N''$, for each complete half cycle of the waveform 680 are averaged within a given 10 second interval to obtain the appropriate feature values.

Finally, the last two features extracted from the waveform 680 are the values of maximum points 696 within each cycle of a waveform 680 and the values of minimum points 698 within each cycle of the waveform 680. Because the waveform 680 is the second derivative of the waveform 600 the maximum and minimum points 696, 698 of the waveform 680 represent the maximum and minimum points of the second derivative of the waveform 600. Preferably, all of the maximum and minimum values are averaged over a 10 second interval to obtain the appropriate feature values.

Once each of the nineteen features described above has been extracted by the CPU 320, additional parameters are obtained involving the relationship between various parameters. For instance, in the present embodiment, the ratio of the heating area to the cooling area is also calculated. The ratio of the heating area to the sum of the heating area and cooling area is calculated. Similar calculations are executed for the positive and negative areas in the first and second derivative waveforms. Similar ratios can also be calculated with respect to the time parameters.

In the present embodiment, values representing each of these features are provided as inputs (known as the input vector) to the multilayer neural network 321 within the main CPU 320. In one advantageous embodiment, the neural network utilizes a non-linear activation function in the hidden layers and a linear activation function for the input and output layers. As well understood in the art, non-linear activation functions for the input and/or the output layers are also suitable, but typically slow down the training process for the neural network.

In the present embodiment, each feature value is also normalized as an input to the neural network 321 to fall within a range of 0 and 1. Advantageously, the minimum expected value of a feature is assigned a normalization value of zero, and the maximum expected value of the feature is assigned the normalization value of one. As understood in the art, other scaled input ranges are possible for inputs to a neural network, such as −1 to 1.

Similarly, the value from the output layer of the neural network ranges from 0 to 1. Thus, a scaling factor relating the value to a cardiac output value in units understood to medical professionals is applied to the output layer value.

It should be understood that other calculations based upon the temperature difference signal, such as the square of the signal, could also provide useful information to input to the neural network processor.

As briefly mentioned above, in order to obtain accurate cardiac output readings based upon the above-described feature inputs, the multi-layer, back-propagation or recurrent neural network within the main CPU 320 is trained. Training a neural network is well understood in the art, and described in several textbooks such as James A. Freeman and David M. Skapura, "Neural Networks, Algorithms, Applications and Programming Techniques," 1991. Therefore, only a brief description of the particular training process used in accordance with the present invention is provided.

In general, training involves individually analyzing many differing input vectors to the neural network, one at a time, and adjusting the weights in the neural network to adjust to an the error between the output of the neural network 321 matches an expected or known output for each input vector.

More specifically for the present case, several thousand input vectors consisting of the parameters delineated above are individually passed to the neural network 321. Initially, the weights between different layers of the neural network 321 are random. Each vector is processed by the neural network 321, and an output is produced. The output value for a given input vector is compared to the actual value (expected value), in this case the measured cardiac output. A difference between the actual value and the output value provides an error signal which is then back propagated through the neural network, as well understood in the art. Based upon this error signal, the neural network adjusts the weights at each level of the network in an attempt to compensate for the error.

This process is repeated for each input vector, until an accurate output value is consistently generated by the neural network. It has been found that, typically, the more significant the relation between the input parameters and the output signal, the easier it is to train the neural network. That is, the neural network produces more accurate output values more quickly when the input parameters are those which bear a significant relation to the desired output parameter.

Figure 11:
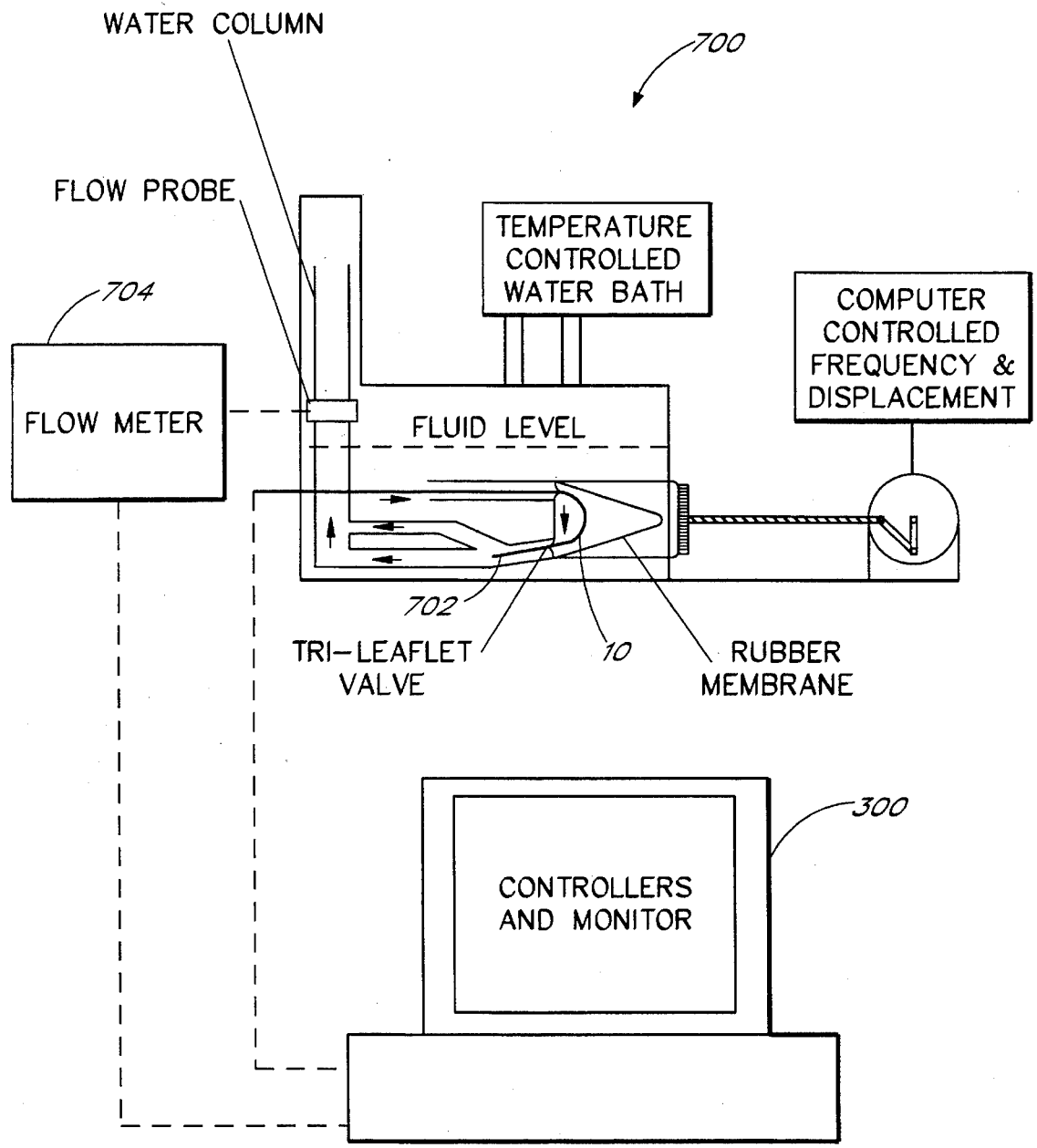
FIG. 11 is a diagrammatic view of a simulated heart circulation system utilized to simulate in vitro fluid volume flow for obtaining test data according to the process of the present invention.

FIG. 11 illustrates a device which may be used to train the neural network used within the present invention. A simulated right heart circulation system 700 includes a heart cavity shaped rubber membrane through which a temperature controlled water/glycerine solution with a specific gravity similar to blood is pumped. The catheter 10 made in accordance with the present invention is connected to the monitor 300 and is positioned so that the distal end of the catheter 10 is within a simulated artery passage 702. A highly accurate electromagnetic flow meter 704 measures fluid flow within the simulated artery passage 702. Simultaneously, the catheter 10, constructed in accordance with the teachings of the present invention, measures fluid flow using the above-described waveform features as an input vector to the neural network. The fluid flow measured by the flow meter 704 provides the expected output value for the neural network. Thus, based upon the measurements taken by the flow meter 704, the error signal is back-propagated through the neural network 321 and the weights are adjusted.

The process is repeated for many input vectors. In other words, input vectors representing many different cardiac conditions are processed with the neural network 321 and the error signal back-propagated to adjust the weights within the network. This process of changing the input vector, comparing the neural network output to the expected output, and making adjustments to the neural network weights continues until the neural network provides an adequate correlation between input vectors and the known output.

It should be understood, that processing methods other than neural networks could be utilized to obtain cardiac output utilizing the temperature difference curves described above. As briefly mentioned above, the selection of the above features is based upon experimentation and studies suggesting that these features relate to the kinetic energy generated by the heart as well as the velocity of the blood flow. The relationship between the temperature difference signal, kinetic energy of the blood, and cardiac output is set forth in the below equations.

Specifically, it is known that the velocity of blood is proportional to the temperature difference signal described above as follows:

$$V = K_1 \left( \frac{K_2}{\Delta t} \right)^{\frac{1}{m}} \quad (1)$$

Where: $K_1$, $K_2$ and m are constants depending upon the characteristics of the liquid, the character of the heat transfer device 24, and the characteristic of the fluid flow (pulsatile, constant, etc.). This relationship is well understood in the art.

It is also understood that kinetic energy $K_E$ relates to velocity and mass as follows:

$$K_E = \tfrac{1}{2} m V^2 \quad (2)$$

Where: m=mass; and V=velocity.
Solving equation (2) for mass (m) results in the following equation:

$$m = \frac{2 K_E}{V^2} \quad (3)$$

Taking the derivative of equation (3) provides the mass flow rate as follows:

$$m' = \frac{\delta \left( \frac{2 K_E}{V^2} \right)}{\delta t} \quad (4)$$

If kinetic energy (or a value corresponding to kinetic energy) and velocity (from equation (1)) are known, then the mass flow rate can be calculated from Equation 4.

Volumetric flow rate (Q) (or cardiac output in the present case) is simply the mass flow rate divided by the density of the fluid as follows:

$$Q = m'_\rho \quad (5)$$

Accordingly, by obtaining the kinetic energy and the velocity, and knowing the density, the volumetric flow rate (cardiac output) can be calculated. In the present embodiment, a neural network is utilized to provide the cardiac output based upon the features described above. The neural network has been observed to provide accurate results. It is believed that the neural network correlates the various features to extract kinetic energy and velocity in order to calculate the cardiac output. Therefore, although a neural network is describe above, any infusateless method which utilizes the temperature difference signal to obtain a value corresponding to cardiac output is also within the scope of the present invention.

It should be noted that the cardiac output values obtained in accordance with the teachings of the present invention are substantially continuous, while the measurements obtained by thermo-dilution are infrequent.

It will be appreciated by one skilled in the art that many obvious modifications can be made to the apparatus and method of the present invention as described herein without departing from its spirit or essential characteristics. Thus, the above description should be construed as merely illustrative and not restrictive. For example, the teachings of the present invention provide apparatus which can be miniaturized and inserted in small areas. Accordingly, the practice of the present invention is particularly suitable for applications in which small volumes of fluid flow are measured. However, those skilled in the art will appreciate that the present invention can be practiced in any situation requiring the direct measurement of fluid volume flow, and thus is not limited to a specific application. For purposes of explanation only, the apparatus and methods described herein are considered in the context of monitoring cardiac output wherein blood volume flow is determined directly and continuously using the monitoring apparatus described above. Furthermore, parameters other than the above-described nineteen features extracted from the temperature difference signal may be used to obtain suitable cardiac output values. Also, specific ones of these features may be selected as inputs to the neural network as called for by the specific conditions of a given application. Accordingly, the limitations of the present invention should be interpreted in light of the appended claims.

We claim:

1. An apparatus for measuring volume flow rate of a liquid having a pulsatile flow within a body lumen, said apparatus comprising:

a heat transfer device in thermal communication with said liquid, said heat device to a first temperature, said first temperature varying with the pulsatile flow of said liquid, wherein said heat transfer device comprises a thermal coil;

a first temperature sensor adapted to be in thermal communication with said heat transfer device to measure the temperature of said heat transfer device, said first temperature sensor having a first output with a first output signal indicative of the temperature of said heat transfer device;

a second temperature sensor adapted to be in thermal contact with said liquid to measure a native temperature of said liquid, said second temperature sensor having a second output with a second output signal indicative of the native temperature of said liquid;

a comparator which responds to said first output signal and said second output signal to provide a temperature difference signal representing the difference in temperature between said native temperature of said liquid and the temperature of said heat transfer device;

a signal processing unit for extracting pre-specified features from said temperature difference signal; and a neural network responsive to said pre-specified features as input parameters and configured to output volume flow rate of said liquid.

2. An apparatus as defined in claim 1, wherein said heat transfer device further comprises a thermally conductive layer interposed between said thermal coil and said first temperature sensor.

3. An apparatus for measuring volume flow rate of a liquid having a pulsatile flow within a body lumen, said apparatus comprising:.
- a heat transfer device in thermal communication with said liquid, said heat transfer device responsive to a low power electrical signal to heat said heat transfer device to a first temperature, said first temperature varying with the pulsatile flow of said liquid, and wherein said heat transfer device comprise a generally tubular thermally conductive layer and a thermal coil wrapped about said generally tubular thermally conductive layer to form a generally tubular heat transfer device;
- a first temperature sensor adapted to be in thermal communication with said heat transfer device to measure the temperature of said heat transfer device, said first temperature sensor having a first output with a first output signal indicative of the temperature of said heat transfer device;
- a second temperature sensor adapted to be in thermal contact with said liquid to measure a native temperature of said liquid, said second temperature sensor having a second output with a second output signal indicative of the native temperature of said liquid;
- a comparator which responds to said first output signal and said second output signal to provide a temperature difference signal representing the difference in temperature between said native temperature of said liquid and the temperature of said heat transfer device;
- a signal processing unit for extracting pre-specified features from said temperature difference signal; and
- a neural network responsive to said pre-specified features as input parameters and configured to output volume flow rate of said liquid.

4. An apparatus as defined in claim 3, wherein a cushioning sheet is positioned adjacent said second temperature sensor to apply pressure on said second temperature sensor so as to improve thermal contact between said thermally conductive layer and said second temperature sensor.

5. A method of detecting volume flow rate of a liquid within a body lumen, said method comprising the steps of:
- detecting a first temperature of a heat transfer device which is in thermal contact with said liquid, said first temperature varying with the flow of the liquid past the heat transfer device;
- detecting a second native temperature of said liquid;
- generating a temperature difference signal based upon the first temperature and the second temperature;
- extracting pre-specified features from said temperature difference signal, wherein said extracted features include: frequency, pulse time, average temperature of said difference signal, cooling area, heating area, cooling time and heating time;
- providing said pre-specified features to a neural network responsive to said pre-specified features as input parameters and configured to output volume flow rate of said liquid; and
- outputting said volume flow rate of said liquid.

6. A method of detecting volume flow rate of a liquid within a body lumen, said method comprising the steps of:
- detecting a first temperature of a heat transfer device which is in thermal contact with said liquid, said first temperature varying with the flow of the liquid past the heat transfer device;
- detecting a second native temperature of said liquid;
- generating a temperature difference signal based upon the first temperature and the second temperature;
- extracting pre-specified features from said temperature difference signal, wherein said extracting step further comprises the steps of taking first and second derivatives of said temperature difference signal and extracting additional ones of said pre-specified features from the first and second derivatives of said temperature difference signal and, wherein said additional ones of said pre-specified features include: positive area in the first derivative of the signal, negative area in the first derivative of the signal, time of the positive area in the first derivative of the signal, time of the negative area in the first derivative of the signal, the value of the maximum point of the first derivative of the signal, the value of the minimum point of the first derivative of the signal, positive area in the second derivative of the signal, negative area in the second derivative of the signal, time of the positive area in the second derivative of the signal, time of the negative area in the second derivative of the signal, the value of the maximum point of the second derivative of the signal, and the value of the minimum point of the second derivative of the signal;
- providing said pre-specified features to a neural network responsive to said pre-specified features as input parameters and configured to output volume flow rate of said liquid; and
- outputting said volume flow rate of said liquid.

7. A cardiac monitoring system for measuring cardiac output within a blood vessel, said monitoring system comprising:
- a catheter having catheter body with a distal end and a proximal end, said catheter comprising:
  - a proximal temperature sensor positioned along the catheter body, said proximal temperature sensor adapted to measure the temperature of blood within said blood vessel when said catheter is positioned in a body lumen, said proximal temperature sensor having an output indicative of a first blood temperature;
  - a distal temperature sensor positioned along said catheter body and in thermal contact with a heat transfer device which is adapted to be in thermal contact with blood when said catheter is positioned within a body lumen, said distal temperature sensor having an output of a second temperature signal indicative of the temperature of the heat transfer device;
- a central processing unit which communicates with said first and second temperature sensors of said catheter, said central processing unit including:
- a comparator which responds to said first temperature signal and said second temperature signal to provide a temperature difference signal;
- a differentiator which forms derivatives of said temperature difference signal;
- a signal processing unit for extracting pre-specified features from said temperature difference signal and from said derivative signals; and
- a processor responsive to said pre-specified features as input parameters and configured to output a value representative of cardiac output of blood within said blood vessel, wherein said processor is further responsive to said temperature difference signal to provide a heart rate.

\* \* \* \* \*

UNITED STATES PATENT AND TRADEMARK OFFICE
CERTIFICATE OF CORRECTION

PATENT NO. : 5,509,424

DATED : April 23, 1996

INVENTOR(S) : Ammar

It is certified that error appears in the above-identified patent and that said Letters Patent is hereby corrected as shown below:

```
Column 18, line 42, change "heat device to a first" to --heat
transfer device responsive to a low power electrical signal to
heat said heat transfer device to a first--.
```

Signed and Sealed this

Twentieth Day of May, 1997

*Attest:*

BRUCE LEHMAN

*Attesting Officer*     *Commissioner of Patents and Trademarks*